United States Patent
Lin et al.

(10) Patent No.: US 11,707,461 B2
(45) Date of Patent: Jul. 25, 2023

(54) N-FORMYL VORTIOXETINE AND PREPARATION METHOD THEREOF AND SOLID PREPARATION OF VORTIOXETINE

(71) Applicant: Zhejiang Huahai Pharmaceutical Co., Ltd, Zhejiang (CN)

(72) Inventors: Jinsheng Lin, Zhejiang (CN); Tianpei Huang, Zhejiang (CN); Feifei Lan, Zhejiang (CN); Xiaoyan Xu, Zhejiang (CN); Libin Hu, Zhejiang (CN); Dan Li, Zhejiang (CN); Wenquan Zhu, Zhejiang (CN); Min Li, Zhejiang (CN); Zhiyun Wang, Zhejiang (CN)

(73) Assignee: ZHEJIANG HUAHAI PHARMACEUTICAL CO., LTD, Zhejiang (CN)

( * ) Notice: Subject to any disclaimer, the term of this patent is extended or adjusted under 35 U.S.C. 154(b) by 69 days.

(21) Appl. No.: 16/647,847

(22) PCT Filed: Sep. 20, 2017

(86) PCT No.: PCT/CN2017/102470
§ 371 (c)(1),
(2) Date: Mar. 16, 2020

(87) PCT Pub. No.: WO2019/056211
PCT Pub. Date: Mar. 28, 2019

(65) Prior Publication Data
US 2020/0306245 A1  Oct. 1, 2020

(51) Int. Cl.
*A61K 31/4965* (2006.01)
*A61K 47/38* (2006.01)

(52) U.S. Cl.
CPC .......... *A61K 31/4965* (2013.01); *A61K 47/38* (2013.01)

(58) Field of Classification Search
CPC .................................................. A61K 31/4965
See application file for complete search history.

(56) References Cited

FOREIGN PATENT DOCUMENTS

| CN | 105017175 A | * | 4/2014 | |
|---|---|---|---|---|
| CN | 104230852 A | | 12/2014 | |
| CN | 105017175 B | | 11/2015 | |
| CN | 105339361 A | | 2/2016 | |
| GB | 2557867 | * | 11/2015 | ......... C07D 295/096 |
| WO | 2014191548 A1 | | 12/2014 | |
| WO | WO 2015/079018 | * | 6/2015 | ......... C07D 295/096 |
| WO | 2017162536 A1 | | 9/2017 | |
| WO | WO 2017162536 | * | 9/2017 | ......... C07D 295/096 |

OTHER PUBLICATIONS

Nascimento, 2017 International Nuclear Atlantic Conference—INAC 2017 Belo Horizonte, MG, Brazil, Oct. 22-27, 2017.*
Extended European Search Report for European Patent Application No. 17925919.7 dated Jun. 25, 2020; 5 pgs.
China Intellectual Property Office; China Application No. 201780093994.8; First Office Action; dated Oct. 11, 2022; 5 pages.

* cited by examiner

*Primary Examiner* — Nizal S Chandrakumar
(74) *Attorney, Agent, or Firm* — Umberg Zipser LLP

(57) ABSTRACT

Disclosed is N-formyl vortioxetine, and also disclosed is a method for preparing the N-formyl vortioxetine and a stable solid preparation of vortioxetine.

3 Claims, 2 Drawing Sheets

N-FORMYL VORTIOXETINE AND PREPARATION METHOD THEREOF AND SOLID PREPARATION OF VORTIOXETINE

FIELD OF THE INVENTION

The present invention relates to N-formyl vortioxetine and preparation method thereof and solid preparation of vortioxetine.

BACKGROUND OF THE INVENTION

Vortioxetine, trade name Brintellix®, is developed and sold jointly by Takeda Pharmaceuticals and Lundbeck Pharmaceuticals, for the treatment of major depressive disorder. Its chemical name is 1-[2-(2,4-methylphenylthio)phenyl] piperazine, with a molecular formula of $C_{18}H_{22}N_2S$, molecular weight of 298.45, and its structural formula is as follows:

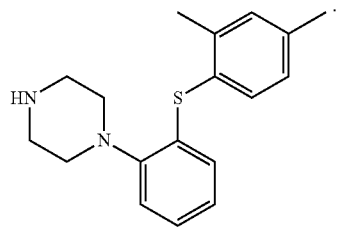 [SMILES: Cc1ccc(Sc2ccccc2N2CCNCC2)c(C)c1]

Impurity research is an important part of drug research and development. Throughout drug research and development, the presence of impurities directly affects the safety, effectiveness and quality controllability of drugs.

SUMMARY OF THE INVENTION

The inventors unexpectedly discovered an unknown impurity during prescription research of vortioxetine solid preparation, especially vortioxetine hydrobromide tablets and vortioxetine hydrobromide sustained-release tablets. When the condition parameters for the preparation of vortioxetine solid preparation are not well controlled, the content of such unknown impurity can even reach more than 0.5%, which exceeds the limit of 0.2% for single impurity content in a preparation product. Therefore, there is an urgent need to determine the specific structure of the impurity and develop a method for quickly and economically preparing the impurity compound. This has great practical significance for the formulation development, stability research and analytical method development of vortioxetine solid preparation.

The first aspect of the present invention provides N-formyl vortioxetine (I), which is a new vortioxetine impurity, and it has a structural formula shown by the following formula (I):

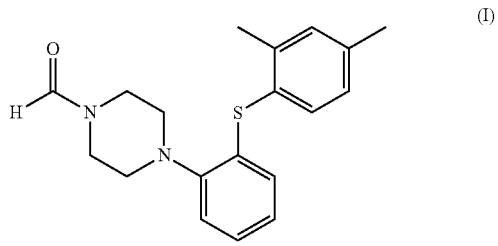 [SMILES: Cc1ccc(Sc2ccccc2N2CCN(C=O)CC2)c(C)c1]

The structure of N-formyl vortioxetine is characterized as follows: its [M+H$^+$] accurate molecular weight is 327.1535, as determined by high resolution mass spectrometry (HRMS) with a matching error of 2.75 ppm, and thus the corresponding molecular formula is $C_{19}H_{22}N_2OS$, as shown in FIG. 1. The determined molecular weight is almost identical to the theoretical exact molecular weight of 327.1526 for N-formyl vortioxetine.

The $^1$H-NMR and $^{13}$C-NMR data of N-formyl vortioxetine are summarized in Tables 1 and 2.

TABLE 1

$^1$H-NMR spectrum data of N-formyl vortioxetine

| Proton Type | Chemical Shift (ppm) | Peak Pattern | NO. Assignment H | Proton Number |
|---|---|---|---|---|
| C—H | 2.32 | s | H-3 | 3 |
| C—H | 2.37 | s | H-6 | 3 |
| C—H | 3.04 | t | H-18 | 2 |
| C—H | 3.08 | t | H-15 | 2 |
| C—H | 3.57 | t | H-16 | 2 |
| C—H | 3.75 | t | H-17 | 2 |
| C—H | 6.52 | d | H-10 | 1 |
| C—H | 6.91 | t | H-11 | 1 |
| N—H | 7.02 | d | H-13 | 1 |
| C—H | 7.04 | d | H-7 | 1 |
| N—H | 7.08 | t | H-12 | 1 |
| C—H | 7.16 | s | H-4 | 1 |
| C—H | 7.37 | d | H-8 | 1 |
| C—H | 8.10 | s | H-19 | 1 |

TABLE 2

$^{13}$C-NMR spectrum data of N-formyl vortioxetine

| Chemical Shift (ppm) | C Atom Type | C Number | NO. Assignment C |
|---|---|---|---|
| 20.7 | CH$_3$ | 1 | C-3 |
| 21.3 | CH$_3$ | 1 | C-6 |
| 40.7 | CH$_2$ | 1 | C-17 |
| 46.4 | CH$_2$ | 1 | C-16 |
| 51.2 | CH$_2$ | 1 | C-18 |
| 52.5 | CH$_2$ | 1 | C-15 |
| 120.2 | CH | 1 | C-13 |
| 125.1 | CH | 1 | C-11 |
| 125.7 | CH | 1 | C-12 |
| 126.4 | CH | 1 | C-10 |
| 127.6 | C | 1 | C-1 |
| 128.0 | CH | 1 | C-7 |
| 131.9 | CH | 1 | C-4 |
| 134.8 | C | 1 | C-9 |
| 136.2 | CH | 1 | C-8 |
| 139.5 | C | 1 | C-5 |
| 142.5 | C | 1 | C-2 |
| 148.5 | C | 1 | C-14 |
| 161.1 | C | 1 | C-19 |

The $^1$H-NMR and $^{13}$C-NMR spectrum are shown in FIGS. 2 and 3, and the No. of C are shown in FIG. 4.

Without being limited to theory, the inventors unexpectedly discovered that the vortioxetine molecule contains an unsubstituted secondary amine as an end group in piperazine ring, and under the condition of long-term storage of vortioxetine solid preparation and relatively extreme high temperature or high humidity, the secondary amine in piperazine ring of vortioxetine easily undergoes rearrangement reactions with reducing sugar excipients contained in the prescription or excipients such as cellulose or cellulose derivatives, thereby attaching a formyl group to the secondary amine group, i.e. resulting in the N-formyl vortioxetine impurity. The possible source of the impurity is as follows:

erazine ring of vortioxetine may also undergo a formylation reaction with impurities such as formic acid, formate or formyl cellulose present in the cellulose or modified cellulose-based excipients in the prescription, thereby attaching a formyl group to the secondary amine An N-formyl vortioxetine impurity can also be produced as above, and the production of the impurity is closely related to the water content in vortioxetine solid preparation and its preparation process.

The second aspect of the present invention provides a method for preparing N-formyl vortioxetine, comprising the following steps:

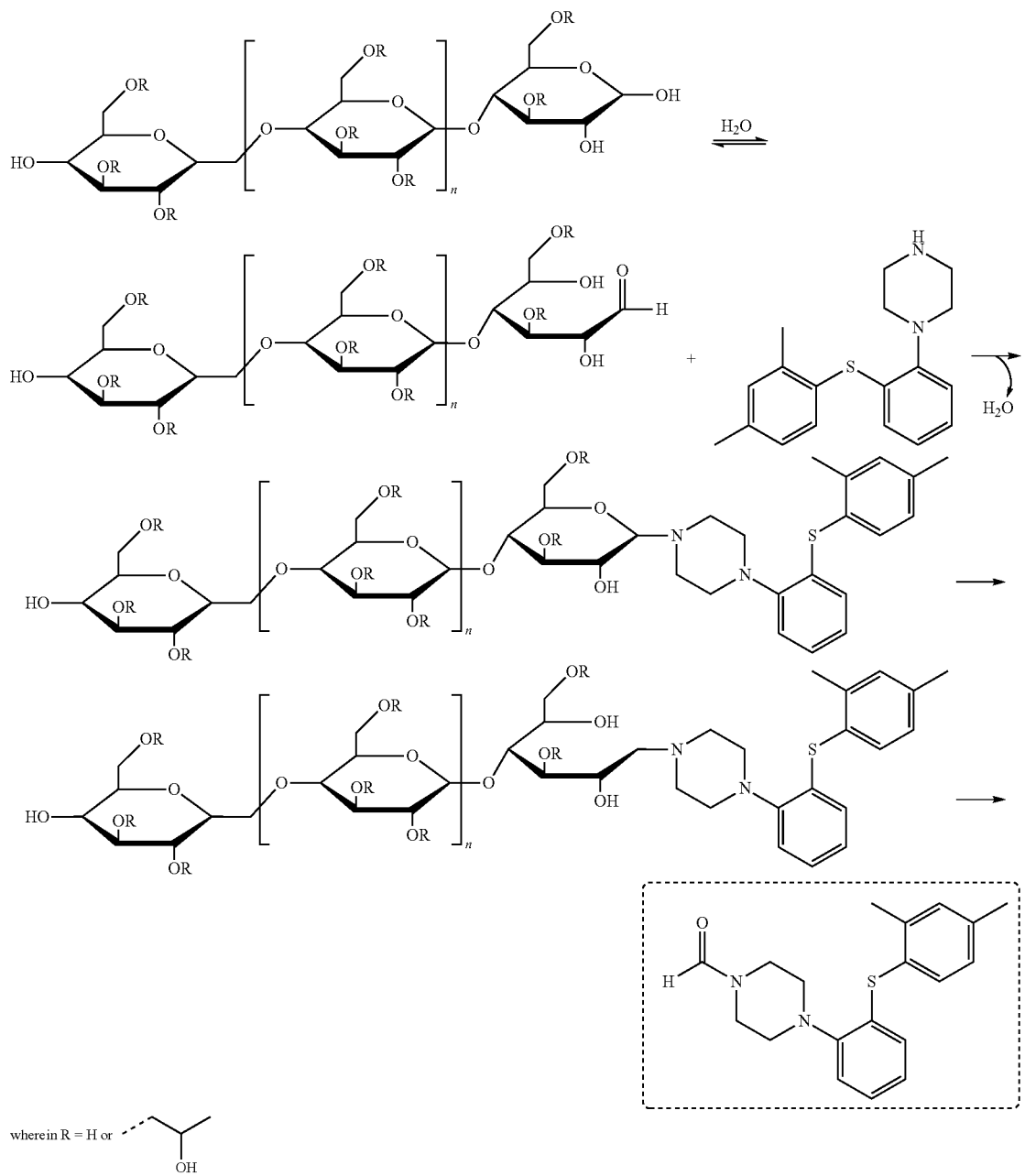

In addition, under the condition of long-term storage of vortioxetine solid preparation and relatively extreme high temperature or high humidity, the secondary amine in pip- (a) adding vortioxetine free base or a salt formed by vortioxetine and acid to a reaction solvent, and then adding a formylating agent;

(b) heating a reaction mixture to 30 to 150° C. for reaction;

(c) isolating a target product of N-formyl vortioxetine after the reaction is complete.

The acid in step (a) may be an inorganic acid or an organic acid. The salt formed by vortioxetine and an acid is selected from the group consisting of vortioxetine hydrobromide, vortioxetine hydrochloride, vortioxetine sulfate, vortioxetine hydrosulfate, vortioxetine mesylate, vortioxetine citrate, vortioxetine tartrate, vortioxetine maleate, vortioxetine malate, vortioxetine fumarate, vortioxetine p-toluene sulfonate, vortioxetine formate, vortioxetine acetate, vortioxetine propionate, vortioxetine pamoate, more preferably vortioxetine hydrobromide.

In step (a), the purity of the vortioxetine free base or the salt formed by vortioxetine and acid is preferably 90% or more, and more preferably 99% or more.

The reaction solvent in step (a) is water, a polar organic solvent, or a mixture thereof The polar organic solvent is preferably selected from formic acid, N, N-dimethylformamide or dimethylsulfoxide.

The formylating agent used in step (a) is selected from the group consisting of formic acid, methyl formate, ethyl formate, propyl formate, isopropyl formate, n-butyl formate, isobutyl formate, tert-butyl formate, benzyl formate, $C_1$-$C_5$ alkyl substituted benzyl formate, phenyl formate, $C_1$-$C_5$ alkyl substituted phenyl formate, or any mixture or combination thereof selected from the group consisting of formic acid and acetic anhydride, formic acid and trifluoroacetic anhydride, formic acid and methyl chloroformate, formic acid and ethyl chloroformate, formic acid and n-propyl chloroformate, formic acid and isopropyl chloroformate, formic acid and n-butyl chloroformate, formic acid and t-butyl chloroformate, formic acid and benzyl chloroformate.

The formylating agents are preferably formic acid, methyl formate, ethyl formate, benzyl formate, or a mixture of formic acid and acetic anhydride.

When the formylating agent in step (a) is formic acid, the volume-mass ratio of the formylating reagent to the vortioxetine free base or the salt formed by vortioxetine and acid is 0.1 to 100:1 ml/g, preferably 5 to 20:1 ml/g. When the formylating reagent is a reagent other than formic acid or a mixture of formic acid and other reagents, the molar ratio of the formylating reagent to the vortioxetine free base or the salt formed by vortioxetine and acid is 0.2 to 50:1, preferably 1 to 10:1.

The heating temperature in step (b) is preferably 80 to 110° C., and the heating time is preferably 12 to 18 hours.

According to the method for preparing N-formyl vortioxetine provided by the present invention, after the reaction is complete, the content of the target product of N-formyl vortioxetine in the reaction solution is 55-80%, preferably 60-80%, more preferably 65-80%, further preferably 70-80%, and even more preferably 75-80%. The remaining components are mainly unreacted vortioxetine, and the difficulty of separating the target product is greatly reduced. However, the content of the impurity in the sample obtained by degradation of the conventional vortioxetine solid preparation is only about 0.5%, which is difficult to separate and thus failing to carry out corresponding follow-up research.

The purity of the N-formyl vortioxetine obtained according to the preparation method of the present invention is 90% or more, preferably 95% or more, and more preferably 99% or more.

N-formyl vortioxetine according to the present invention is used as an impurity reference substance in the detection of vortioxetine solid preparation.

According to the third aspect of the present invention, the present invention also provides a stable vortioxetine solid preparation comprising vortioxetine or a pharmaceutically acceptable salt thereof, and a pharmaceutically acceptable excipient, wherein the content of N-formyl vortioxetine is not more than 0.5% of the labeled amount of vortioxetine, and preferably not more than 0.2% of the labeled amount of vortioxetine, more preferably not more than 0.1% of the labeled amount of vortioxetine after the vortioxetine solid preparation is left for 6 months under the conditions of a temperature of 40° C. and a relative humidity of 75%.

The vortioxetine solid preparation according to the present invention comprises vortioxetine or a pharmaceutically acceptable salt thereof, and a pharmaceutically acceptable excipient, wherein the excipient does not comprise a reducing sugar material such as glucose, fructose, galactose, lactose, maltose, etc.

Preferably, the excipient does not comprise cellulose or cellulose derivatives. Preferably, when the excipient comprises cellulose or cellulose derivatives, the solid preparation of vortioxetine must be prepared by a dry granulation process. The cellulose includes powdered cellulose, microcrystalline cellulose, silicified microcrystalline cellulose, and the cellulose derivatives include hydroxypropyl cellulose, hydroxypropyl methyl cellulose, methyl cellulose, carboxymethyl cellulose, sodium carboxymethyl cellulose, calcium carboxymethyl cellulose or croscarmellose sodium.

The voltioxetine solid preparation according to the present invention includes dosage forms such as tablets, capsules, granules, and the like.

The present invention also provides a method for preparing the vortioxetine solid preparation, which adopts a dry granulation process and includes the following steps:

uniformly mixing vortioxetine or a pharmaceutically acceptable salt thereof and a pharmaceutically acceptable excipient;

pressing the mixture of step 1) into a compact;

converting the compact into granules;

compressing the granules into tablets or filling the granules into capsules.

The present invention also provides a method for controlling the quality of the vortioxetine solid preparation, wherein N-formyl vortioxetine is used as an impurity reference substance. The preferred quality control method includes the following steps: weighing an appropriate amount of N-formyl vortioxetine and dissolving it in a diluent to prepare an impurity reference substance solution with an appropriate concentration; and then qualitatively or quantitatively determining the impurities of N-formyl vortioxetine comprised in the solid preparation sample of vortioxetine by reversed-phase liquid chromatography.

The N-formyl vortioxetine discovered by the present invention has important application significance in the prescription research, stability research and analysis method development of vortioxetine solid preparation. In addition, the N-formyl vortioxetine discovered by the present invention makes it possible to control the quality of the solid preparation of vortioxetine more easily and intuitively. In addition, the method for preparing N-formyl vortioxetine according to the present invention has a low process cost, easy control, and easy availability of raw materials; and the obtained product has stable quality and high yield.

The vortioxetine solid preparation provided by the invention has good stability, lower impurity content and less degradation of the main drug during production and storage, which is helpful to improve safety and effectiveness of the vortioxetine solid preparation.

DETAILED DESCRIPTION OF THE INVENTION

Figure 1:
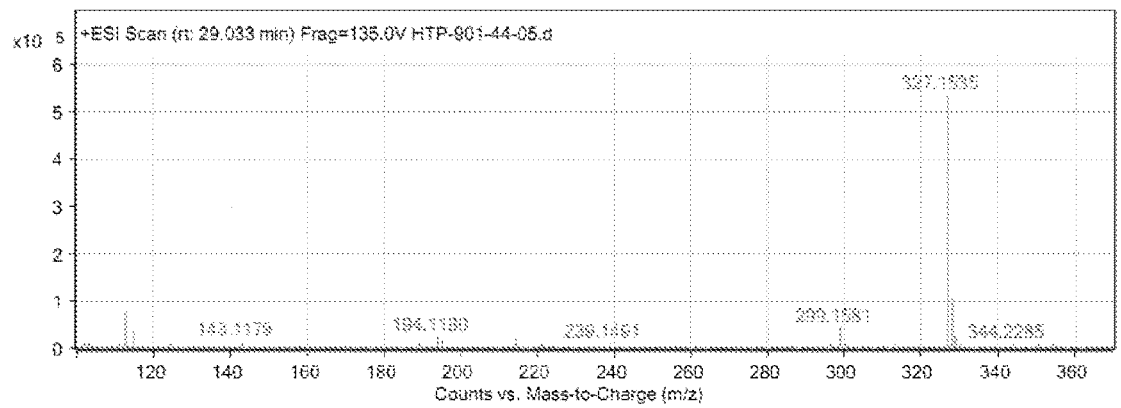
FIG. 1 shows high resolution mass spectrometry (HRMS) data of N-formyl vortioxetine prepared by the present invention.
Figure 2:
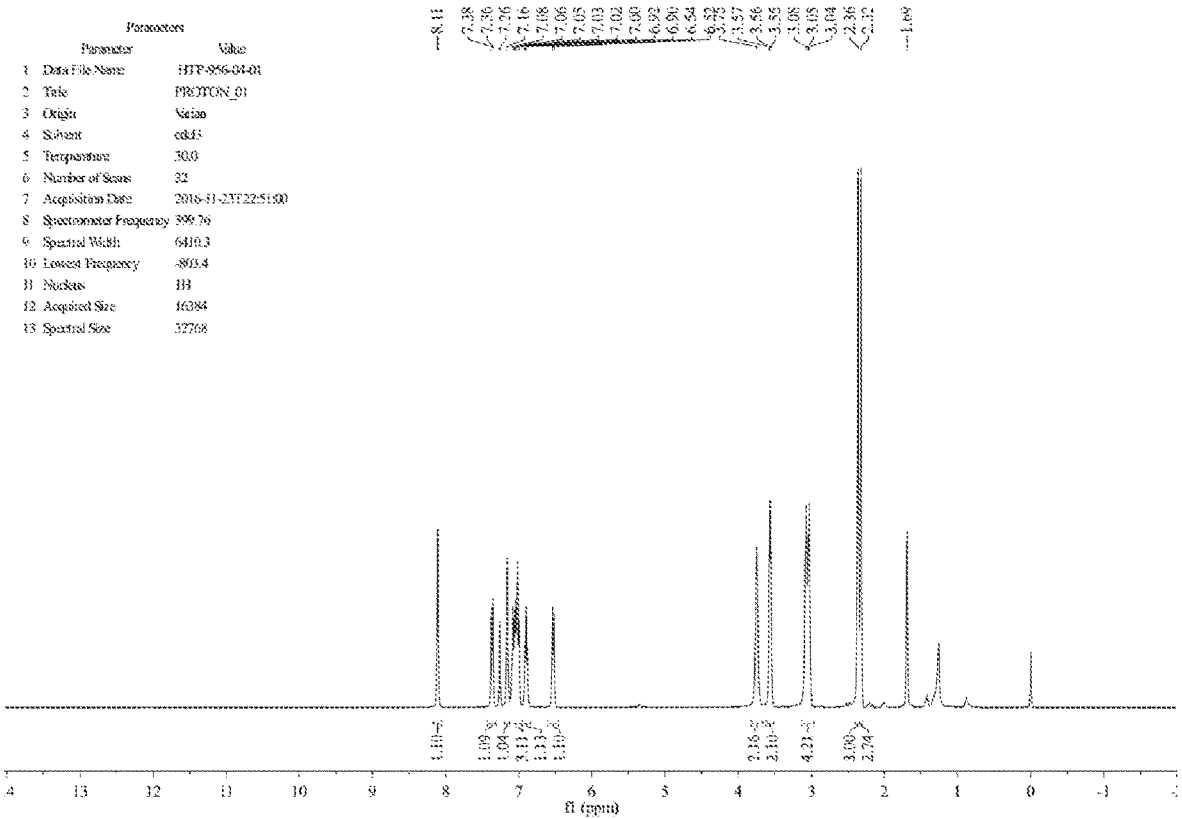
FIG. 2 is $^1$H-NMR spectrum pattern of N-formyl vortioxetine prepared by the present invention.
Figure 3:
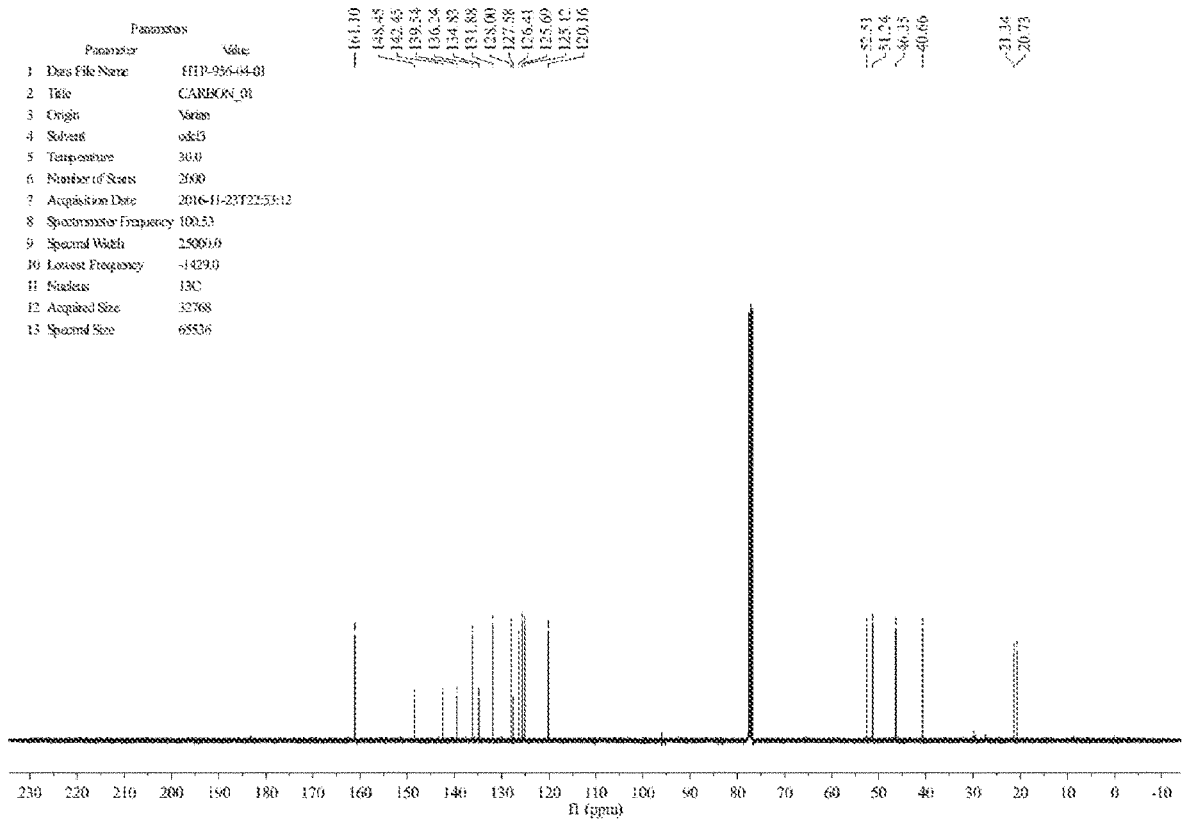
FIG. 3 is $^{13}$C-NMR spectrum pattern of N-formyl vortioxetine prepared by the present invention.
Figure 4:
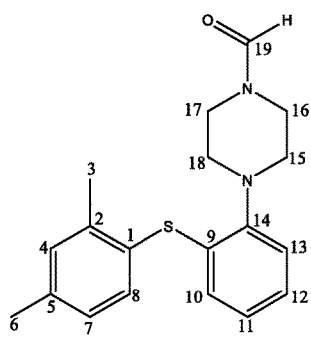
FIG. 4 is the atom number in the structural formula of the N-formyl vortioxetine prepared by the present invention.

The present invention is further illustrated below by examples.

EXAMPLE 1

1 g of vortioxetine hydrobromide was added to 10 mL of formic acid, heated to 100° C., and reacted for 18 hours. The reaction solution was monitored by HPLC, and the content of N-formyl vortioxetine in the reaction solution was measured as 75%. The formic acid was distilled off with a rotary evaporator, and then the residue was separated by a column chromatography method [HP-Silica normal phase silica gel, eluent: methylene chloride: methanol=(10:1, V/V)] to obtain 0.60 g of N-formyl vortioxetine, with an HPLC purity of 99.8% and a yield of 70%.

EXAMPLE 2

1 g of vortioxetine hydrobromide was added to 12 mL of formic acid, heated to 110° C., and reacted for 16 hours. The reaction solution was monitored by HPLC, and the content of N-formyl vortioxetine in the reaction solution was measured as 80%. The formic acid was removed with a lyophilizer, and then the residue was recrystallized with 10 mL of methanol to obtain 0.59 g of N-formyl vortioxetine, with an HPLC purity of 95.7% and a yield of 69%.

EXAMPLE 3

1 g of vortioxetine hydrobromide was added to 12 mL of formic acid, heated to 90° C., and reacted for 16 hours. The reaction solution was monitored by HPLC, and the content of N-formyl vortioxetine in the reaction solution was measured as 71%. After most of the formic acid was distilled off with a rotary evaporator, the residue was diluted with 80 mL of water. Then, the pH was adjusted to about 9 with sodium carbonate, and solids precipitated at this time. The precipitated solid was separated by a column chromatography method [HP-Silica normal phase silica gel, eluent: methylene chloride: methanol=(9:1, V/V)] to obtain 0.47 g of N-formyl vortioxetine, with an HPLC purity of 99.6% and a yield of 55%.

EXAMPLE 4

1 g of vortioxetine free base was added to 20 mL of water-formic acid (1:1, V/V), heated to 90° C., and reacted for 20 hours. The reaction solution was monitored by HPLC, and the content of N-formyl vortioxetine in the reaction solution was measured as 74%. After most of the formic acid was distilled off with a rotary evaporator, the residue was diluted with 80 mL of water. Then, the pH was adjusted to about 9 with sodium carbonate, and solids precipitated at this time. The solid was recrystallized with 12 mL of ethanol to obtain 0.59 g of N-formyl vortioxetine, with an HPLC purity of 93.8% and a yield of 54%.

EXAMPLE 5

1 g of vortioxetine free base was added to 12 mL of N,N-dimethylformamide, then 2 mL of methyl formate was added, heated to 90° C., and reacted for 20 hours. The reaction solution was monitored by HPLC, and the content of N-formyl vortioxetine in the reaction solution was measured as 66%. The N,N-dimethylformamide and unreacted methyl formate were removed by a lyophilizer, and then the residue was separated by a column chromatography method [HP-Silica normal phase silica gel, eluent: methylene chloride: methanol=(9:1, V/V)] to obtain 0.57 g of N-formyl vortioxetine, with an HPLC purity of 99.1% and a yield of 52%.

EXAMPLE 6

1 g of vortioxetine free base was added to 12 mL of N,N-dimethylformamide, then 3 mL of ethyl formate was added, heated to 90° C., and reacted for 20 hours. The reaction solution was monitored by HPLC, and the content of N-formyl vortioxetine in the reaction solution was measured as 68%. N,N-dimethylformamide and unreacted ethyl formate were removed by a lyophilizer, and then the residue was recrystallized with 20 mL of ethyl acetate to obtain 0.60 g of N-formyl vortioxetine with an HPLC purity of 91.3% and a yield of 55%.

EXAMPLE 7

1 g of vortioxetine hydrobromide was added to 12 mL of dimethyl sulfoxide, and then 3 mL of benzyl formate was added, heated to 110° C., and reacted for 20 hours. The reaction solution was monitored by HPLC, and the content of N-formyl vortioxetine in the reaction solution was measured as 75%. The dimethyl sulfoxide and unreacted benzyl formate were removed by a lyophilizer, and then the residue was separated by a column chromatography method [HP-Silica normal phase silica gel, eluent: methylene chloride: methanol=(8:1, V/V)] to obtain 0.59 g of N-formyl vortioxetine, with an HPLC purity of 99.5% and a yield of 68%.

EXAMPLE 8

1 g of vortioxetine hydrobromide was added to 12 mL of N,N-dimethylformamide, then 4 mL of benzyl formate was added, heated to 110° C., and reacted for 20 hours. The reaction solution was monitored by HPLC, and the content of N-formyl vortioxetine in the reaction solution was measured as 73%. N,N-dimethylformamide and unreacted benzyl formate were removed by a lyophilizer, and then the residue was recrystallized with 20 mL of ethyl acetate to obtain 0.49 g of N-formyl vortioxetine with an HPLC purity of 90.6% and a yield of 57%.

EXAMPLE 9

1 g of vortioxetine hydrobromide was added to 10 mL of formic acid, and then 5 mL of acetic anhydride was added, heated to 110° C., and reacted for 15 hours. The reaction solution was monitored by HPLC, and the content of N-formyl vortioxetine in the reaction solution was measured as 67%. The formic acid and acetic anhydride were removed by a lyophilizer, and the residue was recrystallized with 10 mL of acetone to obtain 0.44 g of N-formyl vortioxetine, with an HPLC purity of 91.7% and a yield of 51%.

EXAMPLE 10

1 g of vortioxetine free base was added to 10 mL of formic acid, and then 5 mL of acetic anhydride was added, heated to 90° C., and reacted for 20 hours. The reaction solution was monitored by HPLC, and the content of N-formyl vortioxetine in the reaction solution was measured as 61%. The formic acid and acetic anhydride were removed by a lyophilizer, and then the residue was separated by a thin layer chromatography method [HP-Silica normal phase silica gel, eluent: methylene chloride: methanol=(15:1, V/V)] to obtain 0.60 g of N-formyl vortioxetine, with an HPLC purity of 99.1% and a yield of 55%.

EXAMPLE 11

1 g of vortioxetine mesylate was added to 10 mL of formic acid, and then 2.0 mL of phenyl formate was added, heated to 150° C., and reacted for 15 hours. The reaction solution was monitored by HPLC, and the content of N-formyl vortioxetine in the reaction solution was measured as 69%. The formic acid and unreacted phenyl formate were removed by a lyophilizer, and then the target product was separated from the residue by a column chromatography method [HP-Silica normal phase silica gel, eluent: methylene chloride: methanol=(9:1, V/V)] to obtain 0.47 g of N-formyl vortioxetine with high purity, with an HPLC purity of 99.2% and a yield of 57%.

EXAMPLE 12

1 g of vortioxetine citrate was added to 10 mL of formic acid, and then 2.8 mL of a mixture of formic acid and ethyl chloroformate (1:1, V/V) was added, heated to 30° C., and reacted for 14 hours. The reaction solution was monitored by HPLC, and the content of N-formyl vortioxetine in the reaction solution was measured as 74%. The formic acid and unreacted formic acid and ethyl chloroformate were removed by a lyophilizer, and then the target product was separated from the residue by a column chromatography method [HP-Silica normal phase silica gel, eluent: methylene chloride: methanol=(10:1, V/V)] to obtain 0.40 g of N-formyl vortioxetine with high purity, with an HPLC purity of 98.9% and a yield of 60%.

EXAMPLE 13

The formulation of the solid preparation of vortioxetine in this example was shown in the following table:

| | |
|---|---|
| Vortioxetine hydrobromide | 16.95% |
| Microcrystalline cellulose | 15.0% |
| Mannitol | 58.55% |
| Hydroxypropyl cellulose | 3.0% |
| Sodium carboxymethyl starch | 3.0% |
| talcum powder | 2.0% |
| Magnesium stearate | 1.5% |

The method for preparing vortioxetine solid preparation was as follows:
1) sieving vortioxetine hydrobromide, mannitol, hydroxypropyl cellulose, talcum powder, and magnesium stearate, respectively, for later use;
2) uniformly mixing the sieved vortioxetine hydrobromide with microcrystalline cellulose, mannitol, hydroxypropyl cellulose, sodium carboxymethyl starch, and magnesium stearate;
3) adding the mixed powder obtained in step 2) into a dry granulator for dry granulation;
4) uniformly mixing the granules obtained in step 3) with talcum powder and magnesium stearate, for later use;
5) adding the mixed granules obtained in step 4) into the hopper of a tablet press to perform tabletting.

EXAMPLE 14

The formulation of the solid preparation of vortioxetine in this example was shown in the following table:

| | |
|---|---|
| Vortioxetine hydrobromide | 16.95% |
| Mannitol | 71.55% |
| Copovidone | 5.0% |
| Sodium carboxymethyl starch | 3.0% |
| talcum powder | 2.0% |
| Magnesium stearate | 1.5% |

The method for preparing vortioxetine solid preparation is as follows:
1) sieving formulation amount of vortioxetine hydrobromide, mannitol, copovidone, talcum powder, and magnesium stearate, respectively, for later use;
2) uniformly mixing the sieved vortioxetine hydrobromide with mannitol, copovidone, sodium carboxymethyl starch, and magnesium stearate;
3) adding the mixed powder obtained in step 2) into a dry granulator for dry granulation;
4) uniformly mixing the material obtained in step 3) with talcum powder and magnesium stearate, for later use;
5) filling the mixed granules in step 4) into the hollow capsules.

COMPARATIVE EXAMPLE 1

The formulation of the solid preparation of vortioxetine in this example was shown in the following table:

| | |
|---|---|
| Vortioxetine hydrobromide | 16.95% |
| Microcrystalline cellulose | 15.0% |
| Mannitol | 58.55% |
| Hydroxypropyl cellulose | 3.0% |
| Sodium carboxymethyl starch | 3.0% |
| talcum powder | 2.0% |
| Magnesium stearate | 1.5% |

The method for preparing vortioxetine solid preparation was as follows:
1) sieving mannitol, hydroxypropyl cellulose, talcum powder, and magnesium stearate, respectively, for later use;
2) adding vortioxetine hydrobromide, microcrystalline cellulose, and sieved mannitol, hydroxypropyl cellulose, and sodium carboxymethyl starch into a high-shear wet granulator for premixing;
3) adding purified water as a wetting agent into the wet granulator for wet granulation;

4) wet granulating the wet granules obtained in step 3) with a rotary granulator;

5) putting the wet granules obtained in step 4) into a fluidized bed to dry to LOD≤3.0%;

6) adding the dry granules obtained in step 5) and the sieved talcum powder in step 1) to the total mixing tank and mixing them for later use;

7) adding the sieved magnesium stearate to the total mixing tank of step 6) and mixing them for later use 8) adding the mixed granules obtained in step 7) into the hopper of a tablet press to perform tabletting.

Under an accelerated condition (at a temperature of 40° C., and a relative humidity of 75%), the impurity content of vortioxetine hydrobromide tablets prepared in Examples 13, 14 and Comparative Example 1 was examined. The experimental results are shown in the following table:

| Batch | Time | N-formyl vortioxetine | Maximum Single Unknown Impurity | Total Impurities |
|---|---|---|---|---|
| Example 13 | Month 0 | N.D | 0.07% | 0.07% |
| | Month 1 | N.D | 0.09% | 0.14% |
| | Month 3 | <RL(RL = 0.05%) | 0.07% | 0.07% |
| | Month 6 | <RL(RL = 0.05%) | 0.07% | 0.12% |
| Example 14 | Month 0 | N.D | 0.07% | 0.07% |
| | Month 1 | N.D | 0.08% | 0.13% |
| | Month 3 | <RL(RL = 0.05%) | 0.06% | 0.06% |
| | Month 6 | <RL(RL = 0.05%) | 0.07% | 0.12% |
| Comparative Example 1 | Month 0 | <RL(RL = 0.05%) | 0.07% | 0.07% |
| | Month 1 | 0.09% | 0.08% | 0.22% |
| | Month 3 | 0.13% | 0.06% | 0.29% |
| | Month 6 | 0.25% | 0.07% | 0.43% |

The above data shows that, on the one hand, the solid preparation of vortioxetine according to the present invention not only has a significant lower N-formyl vortioxetine content, but also has a significant reduced content of total impurities, compared with the solid preparation of Comparative Example 1. On the other hand, the N-formyl vortioxetine content in the solid preparation of vortioxetine according to the present invention remained below the detection limit, while the solid preparation in Comparative Example 1 contains up to 0.25% of N-formyl vortioxetine after 6 months of storage under the accelerated condition. In addition, the total impurity content of the vortioxetine solid preparation of the present invention is also lower than the total impurity content in Comparative Example 1. Compared with the prior art vortioxetine solid preparation, the vortioxetine solid preparation of the present invention has good stability, lower impurity content and less degradation of the main drug, which is helpful to improve the safety and effectiveness of vortioxetine solid preparation.

EXAMPLE 15

This example illustrates a method for controlling the quality of vortioxetine solid preparation.

Chromatographic conditions
Instrument: HPLC equipped with a UV detector
Column: Waters Xterra MS $C_{18}$, 150×4.6 mm, 3.5 µm
Mobile phase A: Weighing 1.2 g of ammonium acetate and dissolving it in 1000 mL of water and adjusting the pH to 6.0 with glacial acetic acid
Mobile phase B: acetonitrile
Detection wavelength: 250 nm
Flow rate: 1.0 mL/min
Injection volume: 10 µL
Column temperature: 40° C.
Running time: 50 min
Mobile phase gradient:

| Time (min) | A (%, V/V) | B (%, V/V) |
|---|---|---|
| 0 | 80 | 20 |
| 2 | 80 | 20 |
| 18 | 58 | 42 |
| 38 | 10 | 90 |
| 45 | 10 | 90 |
| 46 | 80 | 20 |
| 50 | 80 | 20 |

Diluent: acetonitrile: water=(7:3, V/V)
Blank solution: same as diluent
Preparation of N-formyl vortioxetine control solution: weighing 1 mg of N-formyl vortioxetine and dissolve it in 1 ml of dilution.

Test solution: weighing a few samples of vortioxetine tablets stored under accelerated conditions for three months in Comparative Example 1, and placing them into a volumetric flask with corresponding volume, and adding the diluent to a volume of about ⅔ of the volumetric flask, shaking for 1 h to disperse, sonicating for 5 min to dissolve vortioxetine tablets, cooling to room temperature, adding diluent to reach the mark and uniformly shaking Let it stand for a while, precisely transferring 5 mL of the sample solution to a 50 mL volumetric flask, adding the dilution solution to reach the mark, and uniformly shaking. Then, filtering it through a 0.45 µm PTFE syringe filter, and the filtrate was used as a test solution.

The test solution was detected by the above-mentioned HPLC method, positioned with the N-formyl vortioxetine reference substance solution and quantified by the external standard method. In a vortioxetine tablet stored for 3 months under the accelerated condition, the content of N-formyl vortioxetine was 0.13%.

The above only describes the preferred examples of the present invention in detail.

The present invention is not limited to the above examples, and any changes and modifications to the present invention belong to the protection scope of the present invention.

The invention claimed is:

1. A method for preparing a storage-stable pharmaceutical composition comprising vortioxetine, the method comprising:
    combining vortioxetine or a pharmaceutically acceptable salt thereof, and a pharmaceutically acceptable excipient, wherein the pharmaceutically acceptable excipient is free of a reducing sugar material; and
    dry granulating the vortioxetine or the pharmaceutically acceptable salt thereof, and the pharmaceutically acceptable excipient;
    wherein the storage-stable pharmaceutical composition after storage over 6 months at 40° C. and 75% relative humidity contains no greater than 0.2% of N-formyl vortioxetine;
    wherein the storage-stable pharmaceutical composition consists of following components, based on the total weight of the composition:
vortioxetine hydrobromide 16.95% by weight,
microcrystalline cellulose 15.0% by weight,
mannitol 58.55% by weight,
hydroxypropyl cellulose 3.0% by weight,
sodium carboxymethyl starch 3.0% by weight, talcum powder 2.0% by weight, and
magnesium stearate 1.5% by weight;
  or the storage-stable pharmaceutical composition consists of following components, based on the total weight of the composition:
vortioxetine hydrobromide 16.95% by weight,
mannitol 71.55% by weight,
copovidone 5.0% by weight,
sodium carboxymethyl starch 3.0% by weight,
talcum powder 2.0% by weight, and
magnesium stearate 1.5% by weight.

2. The method of claim 1, wherein:
  the step of combining comprises;
  uniformly mixing vortioxetine or a pharmaceutically acceptable salt thereof and a pharmaceutically acceptable excipient, and
    pressing a mixture of step 1) into a compact;
  the step of dry granulating comprises 3) converting the compact into granules using dry granulation; and
  the method further comprises 4) compressing the granules into tablets or filling the granules into capsules.

3. The method of claim 1, wherein the storage-stable pharmaceutical composition after storage over 6 months at 40° C. and 75% relative humidity contains no greater than 0.1% of N-formyl vortioxetine.

* * * * *